(12) United States Patent
Kusaka

(10) Patent No.: US 7,906,000 B2
(45) Date of Patent: Mar. 15, 2011

(54) ANALYZER AND METHOD OF MANUFACTURING THE SAME

(75) Inventor: Yasuhide Kusaka, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 931 days.

(21) Appl. No.: 11/587,262

(22) PCT Filed: Apr. 22, 2005

(86) PCT No.: PCT/JP2005/007677
§ 371 (c)(1),
(2), (4) Date: Oct. 23, 2006

(87) PCT Pub. No.: WO2005/103663
PCT Pub. Date: Nov. 3, 2005

(65) Prior Publication Data
US 2008/0011605 A1 Jan. 17, 2008

(30) Foreign Application Priority Data
Apr. 23, 2004 (JP) ................................. 2004-128445

(51) Int. Cl.
*G01N 27/26* (2006.01)
(52) U.S. Cl. ......... 204/403.12; 204/403.11; 204/403.01; 422/68.1; 422/82.01
(58) Field of Classification Search .............. 204/403, 204/403.01–403.15; 205/775, 775.5, 777.5, 205/792, 778; 435/4; 422/68.1–98; 600/345–348
See application file for complete search history.

(56) References Cited

U.S. PATENT DOCUMENTS

| | | | |
|---|---|---|---|
| 4,948,355 A * | 8/1990 | Knoll | 425/517 |
| 5,320,732 A | 6/1994 | Nankai et al. | |
| 6,197,494 B1 * | 3/2001 | Oberhardt | 435/4 |
| 6,458,258 B2 | 10/2002 | Taniike et al. | |
| 6,531,040 B2 | 3/2003 | Musho et al. | |
| 6,885,196 B2 | 4/2005 | Taniike et al. | |
| 7,060,168 B2 | 6/2006 | Taniike et al. | |
| 2001/0006149 A1 * | 7/2001 | Taniike et al. | 204/403 |
| 2004/0007461 A1 * | 1/2004 | Edelbrock et al. | 204/403.11 |

FOREIGN PATENT DOCUMENTS

| | | |
|---|---|---|
| JP | 4-357449 | 12/1992 |
| JP | 2001-66279 | 3/2001 |
| JP | 2001-183330 | 7/2001 |
| JP | 2001-249103 | 9/2001 |
| JP | 2003-279526 | 10/2003 |
| WO | WO 02/08743 | 1/2002 |

OTHER PUBLICATIONS

International Search Report for PCT/JP2005/007677, mailed Jun. 14, 2005.

* cited by examiner

*Primary Examiner* — Alexa D Neckel
*Assistant Examiner* — Jennifer Dieterle
(74) *Attorney, Agent, or Firm* — Day Pitney LLP

(57) ABSTRACT

The present invention relates to an analytical tool (X1) including a first and a second plate elements (1, 3), a flow path (4) defined between the plate elements (1, 3) and an exhaust port (31) for discharging gas from the flow path (4). The exhaust port (31) is provided at the first plate element (3) and includes a portion which is offset in a thickness direction of the first plate element (3) from the main body (3A) of the first plate element (3). Preferably, the first plate element (3) includes a projection (51) integrally formed on the first plate element (3) and defining the exhaust port (31).

14 Claims, 22 Drawing Sheets

N2 ⟷ N1

ANALYZER AND METHOD OF MANUFACTURING THE SAME

TECHNICAL FIELD

The present invention relates to an analytical tool used for analyzing a particular component contained in a sample, and a method of manufacturing such an analytical tool.

BACKGROUND ART

An analytical tool designed to analyze a sample by an electrochemical technique or an optical technique is generally used. FIGS. 20-22 of the present application show a glucose sensor 9 (See Patent Document 1, for example) as an example of analytical tool for analyzing a sample by an electrochemical technique.

The illustrated glucose sensor 9 is mounted, in use, to an analyzer, and includes a flow path 90 for moving a sample by a capillary force. Specifically, the glucose sensor 9 includes a substrate 93 provided with a working electrode 91 and a counter electrode 92, and a cover 95 bonded to the substrate via a spacer 94. The flow path 90 is defined by the substrate 93, the spacer 94 and the cover 95 and communicates with the outside through an introduction port 96 and an exhaust port 97. In the glucose sensor 9 having this structure, the sample introduced through the introduction port 96 moves through the flow path 90 by the capillary force generated in the flow path 90 while exhausting gas from the flow path 90 through the exhaust port 97.

In the glucose sensor 9, the exhaust port 97 is provided by forming a through-hole in the cover 95. Specifically, the exhaust port 97 is formed by press working a flat plate to punch out part of the flat plate. However, with the method to punch the flat plate, a punched-out piece is produced in press working. The punched-out piece may not completely separate from the cover 95 and may keep adhering to the cover 95. In such a case, in bonding the cover 95 to the substrate 93, the punched-out piece exists between the substrate 93 and the cover 95. Therefore, the punched-out piece is exposed in the flow path 90 to hinder the movement of the sample in the flow path 90 and adversely affect on the measurement results. Further, with the method to form the exhaust port 97 by punching, even when the punched-out piece is properly separated from the cover 95, the punched-out piece needs to be disposed of, which reduces the manufacturing efficiency. Moreover, in the glucose sensor 9 with an exhaust port 97 formed by punching, the exhaust port 97 opens upward at the upper surface 98 of the glucose sensor 9 (cover 95). Therefore, the user may introduce sample erroneously from the exhaust port 97 instead of introducing from the introduction port 96. In this case again, accurate measurement results cannot be obtained.

Patent Document 1: JP-B-H08-1-0208

DISCLOSURE OF THE INVENTION

An object of the present invention is to provide an analytical tool which can be manufactured with high efficiency and which can reduce analysis errors due to a drawback caused by the manufacturing process or erroneous operation by the user.

According to a first aspect of the present invention, there is provided an analytical tool comprising a first and a second plate elements, a flow path defined between the plate elements and an exhaust port for discharging gas from the flow path. The first plate element includes a flat main body, and the exhaust port is provided at the first plate element and includes a portion which is offset in a thickness direction of the main body.

For instance, the first plate element includes a projection projecting from the main body and integrally formed on the main body, and the projection defines the exhaust port. For instance, the projection is provided by deforming part of the first plate element.

For instance, the projection is in the form of a dome. In this case, for example, the projection includes at least one opening to serve as the exhaust port.

The projection may comprise a cut-and-raised piece. Alternatively, the projection may be in the form of a bridge including a pair of openings which open in a horizontal direction and serve as the exhaust port.

According to a second aspect of the present invention, there is provided a method of manufacturing an analytical tool. The method comprises a first step of forming a first plate member including a flat main body and at least one opening including a portion which opens at a position offset in a thickness direction of the main body, and a second step of bonding a second plate member to the first plate member at a predetermined distance.

For instance, at least one opening is formed by press working a flat plate. For instance, the flat plate may be a plate made of a thermoplastic resin, and the press working may be performed with the flat plate heated to be thermally deformable. In the press working, part of the flat plate may be cut and raised to form the opening.

The first step may comprise forming a cut in the flat plate before the press working is performed. Preferably, in this case, the flat plate is a plate made of a thermoplastic resin, and the press working comprises compressing a portion adjacent to the cut for thermal deformation with the flat plate heated to be thermally deformable.

BEST MODE FOR CARRYING OUT THE INVENTION

Figure 1:
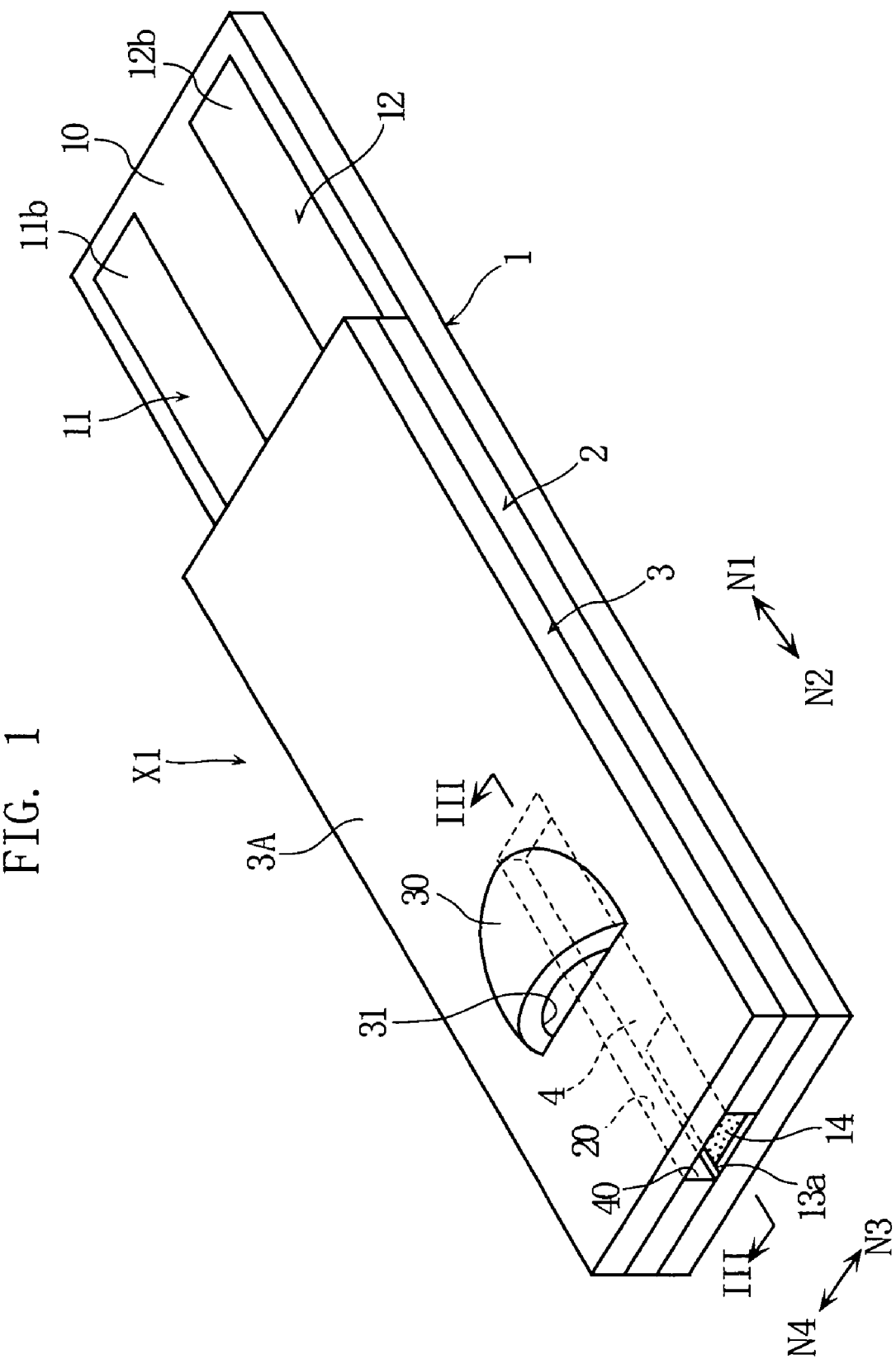
FIG. 1 is an overall perspective view showing a glucose sensor according to a first embodiment of the present invention.
Figure 2:
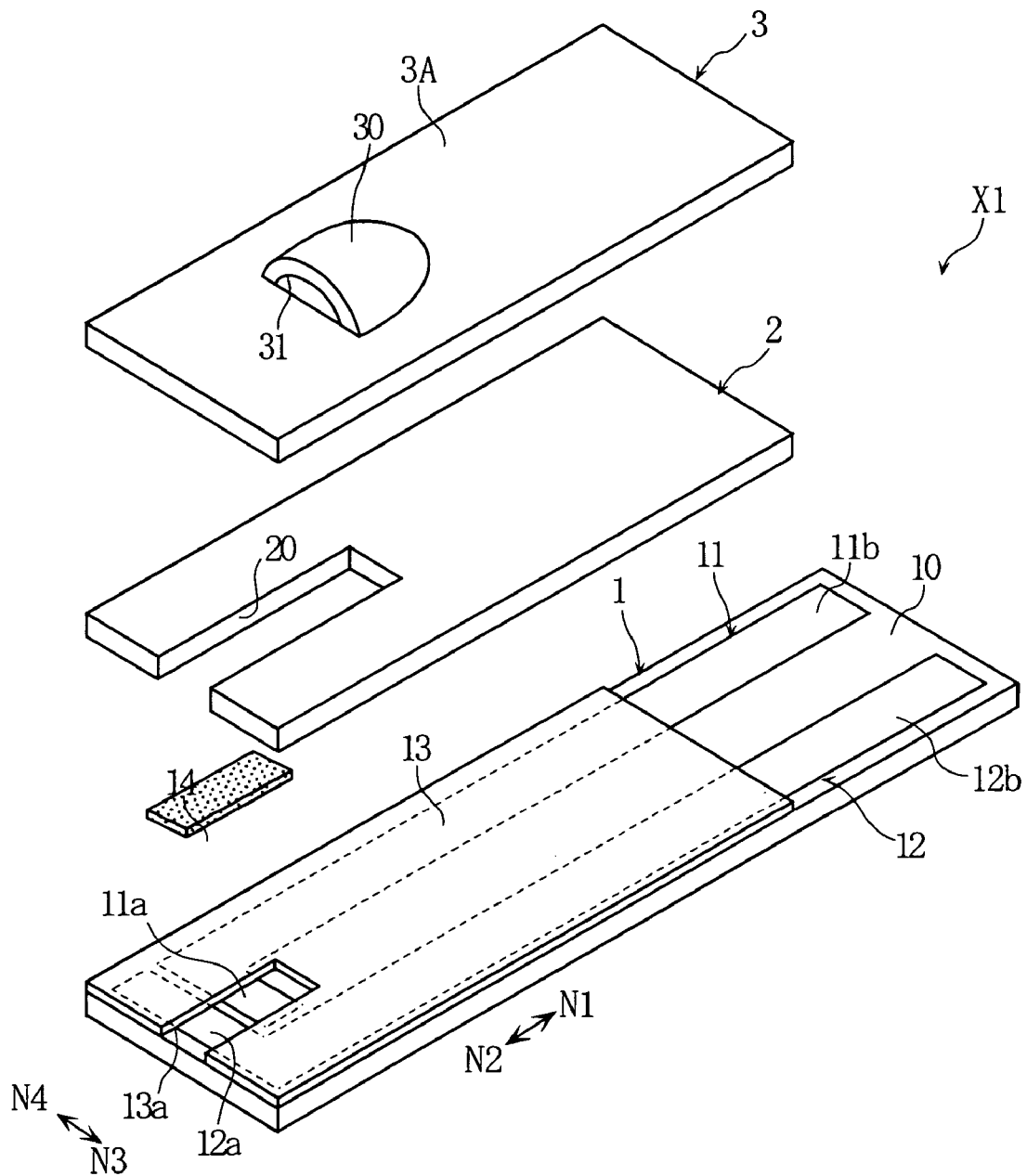
FIG. 2 is an exploded perspective view of the glucose sensor shown in FIG. 1.
Figure 3:
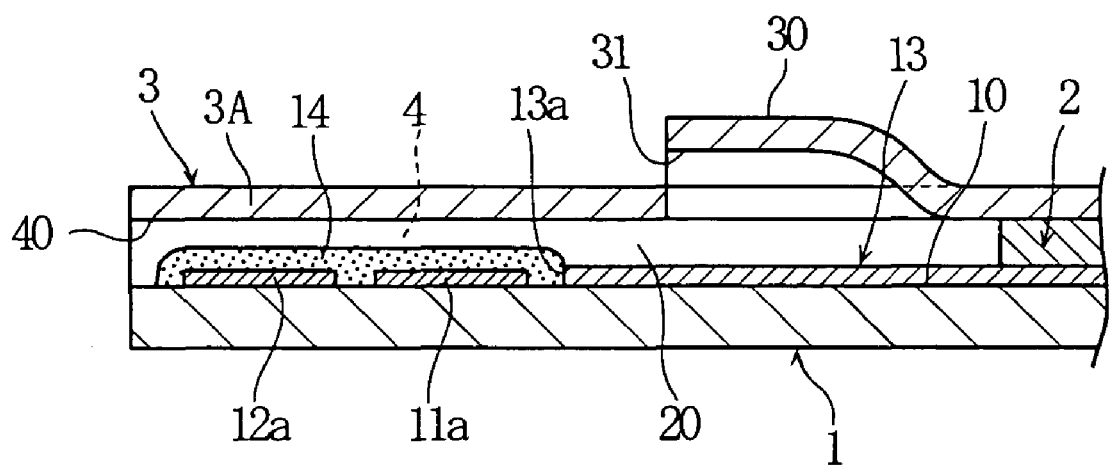
FIG. 3 is a sectional view taken along lines III-III in FIG. 1.

The glucose sensor X1 shown in FIGS. 1-3 is a disposable sensor which is mounted, in use, to a blood glucose level measurer (not shown) for measuring the blood glucose level. The glucose sensor X1 includes a substrate 1 having an elongated rectangular configuration and a cover 3 stacked on the substrate via a spacer 2. In the glucose sensor X1, a capillary 4 extending longitudinally of the substrate 1 (in the direction indicated by arrows N1 and N2 in the figures) is defined by the elements 1-3. The capillary 4 is utilized for moving the blood introduced from an introduction port 40 in the longitudinal direction of the substrate 1 (the direction indicated by arrows N1 and N2 in the figures) by utilizing capillary phenomenon and retaining the introduced blood.

The spacer 2 serves to define the distance from the upper surface 10 of the substrate 1 to the lower surface 30 of the cover 3, i.e., the height of the capillary 4, and may comprise a double-sided tape, for example. The spacer 2 is formed with a slit 20 having an open end. The slit 20 defines the width of the capillary 4, and the open end of the slit 20 serves as the introduction port 40 for introducing blood into the capillary 4.

The cover 3 includes a main body 3A and a projection 30. The main body 3A is the entire portion of the cover 3 except the projection 30 and in the form of a flat plate. The projection 30 is in the form of a dome projecting from the main body 3A and includes an exhaust port 31. The exhaust port 31 is utilized for discharging gas in the capillary 4 to the outside. The exhaust port 31 opens laterally (in the direction indicated by the arrow N2 in the figures) at a position above the main body 3A. The cover 3 may be made of a thermoplastic resin having a high wettability such as vinylon or highly crystalline PVA, for example.

As shown in FIGS. 2 and 3, the substrate 1 is made of an insulating resin such as PET, for example, and a working electrode 11, a counter electrode 12, an insulating film 13 and a reagent portion 14 are provided on the upper surface 10 thereof. Each of the working electrode 11 and the counter electrode 12 is L-shaped as a whole. Specifically, the working electrode 11 and the counter electrode 12 mostly extend in the longitudinal direction of the substrate 1 (the direction indicated by the arrows N1 and N2 in the figures) and respectively include ends 11a and 12a extending in the width direction of the substrate 1 (the direction indicated by the arrows N3 and N4 in the figures) The working electrode 11 and the counter electrode 12 further include ends 11b and 12b, respectively, which serve as terminals for coming into contact with the terminals provided in the blood glucose level measurer (not shown). The working electrode 11 and the counter electrode 12 can be formed by screen printing using conductive carbon ink.

The insulating film 13 covers most part of the working electrode 11 and the counter electrode 12 while exposing the ends 11a, 12a, 11b and 12b of the working electrode 11 and the counter electrode 12. The insulating film 13 is formed with an opening 13a for exposing the ends 11a and 12a of the working electrode 11 and the counter electrode 12. The opening 13a also serves to define the region for forming the reagent portion 14 and has a rectangular configuration extending longitudinally of the substrate 1 (the direction indicated by the arrows N1 and N2 in the figures).

The reagent portion 14 is so arranged as to bridge the ends 11a and 12a of the working electrode 11 and the counter electrode 12 within the opening 13a of the insulating film 13. For instance, the reagent portion includes an electron mediator and a relatively small amount of oxidoreductase. The reagent portion 14 is in the form of a porous solid easily soluble in blood. Therefore, when blood is introduced into the capillary 4, a liquid phase reaction system including an electron mediator, an oxidoreductase and glucose is established in the capillary 4.

For instance, as the oxidoreductase, glucose oxidase (GOD) or glucose dehydrogenase (GDH) maybe used, and typically, PQQGDH is used. For instance, as the electron mediator, ruthenium complex or iron complex may be used, and typically, $[Ru(NH_3)_6]Cl_3$ or $K_3[Fe(CN)_6]$ is used.

With the glucose sensor X1, the blood glucose level can be measured automatically in a blood glucose level measurer (not shown) by mounting the glucose sensor X1 to the blood glucose level measurer (not shown) and supplying blood into the capillary 4 from the introduction port 40 of the glucose sensor X1.

Figure 20:
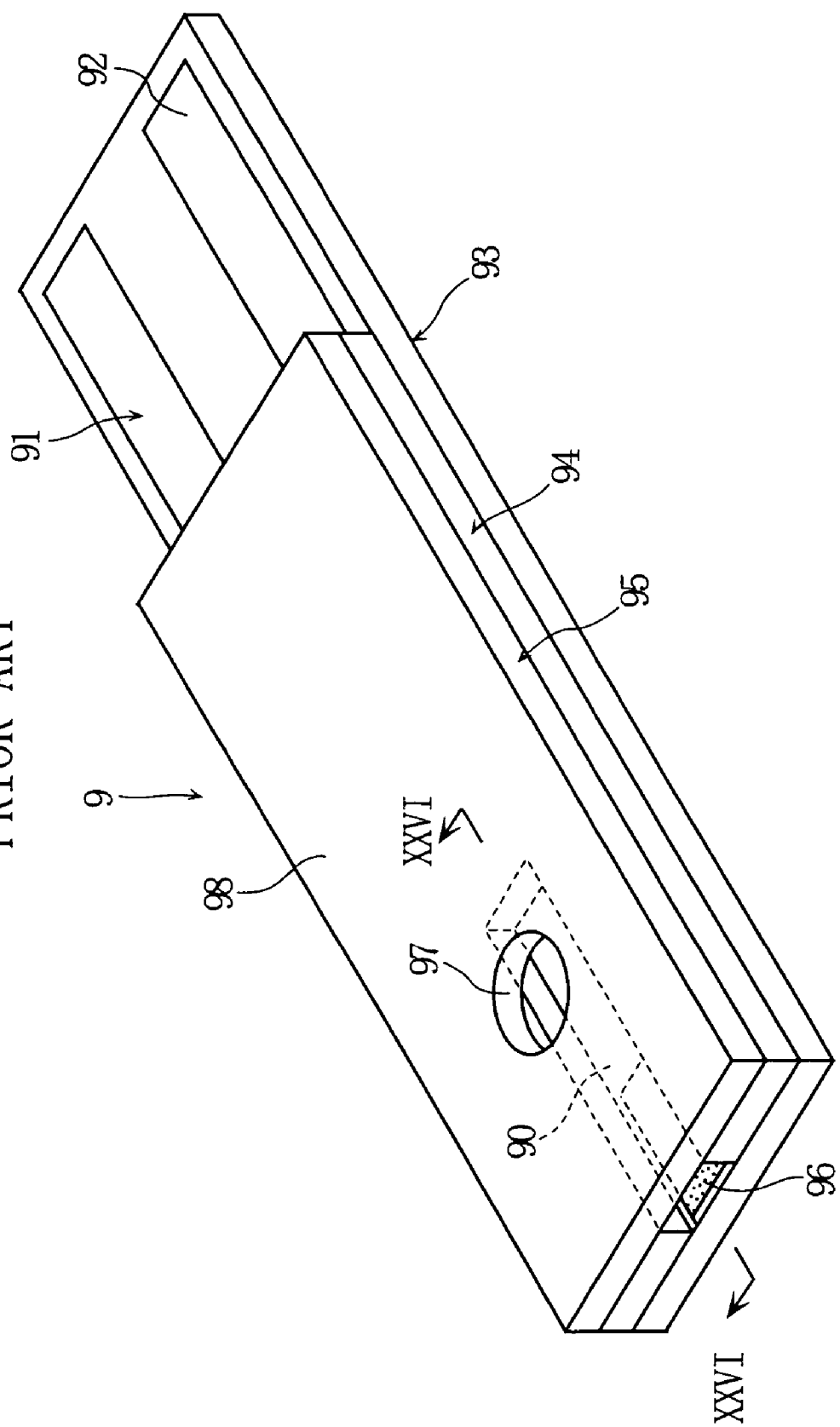
FIG. 20 is an overall perspective view showing an example of conventional glucose sensor.
Figure 21:
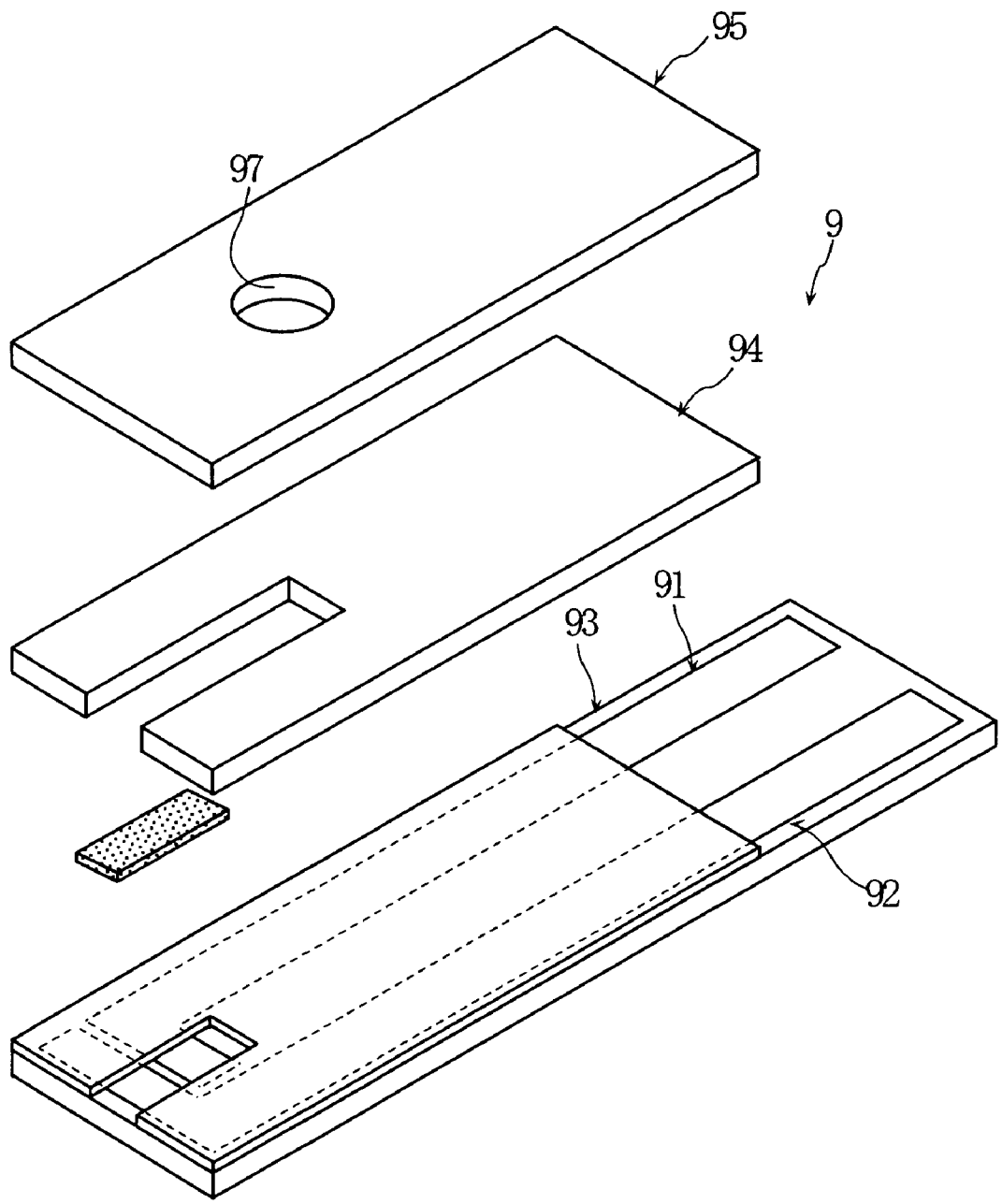
FIG. 21 is an exploded perspective view of the glucose sensor shown in FIG. 20.
Figure 22:
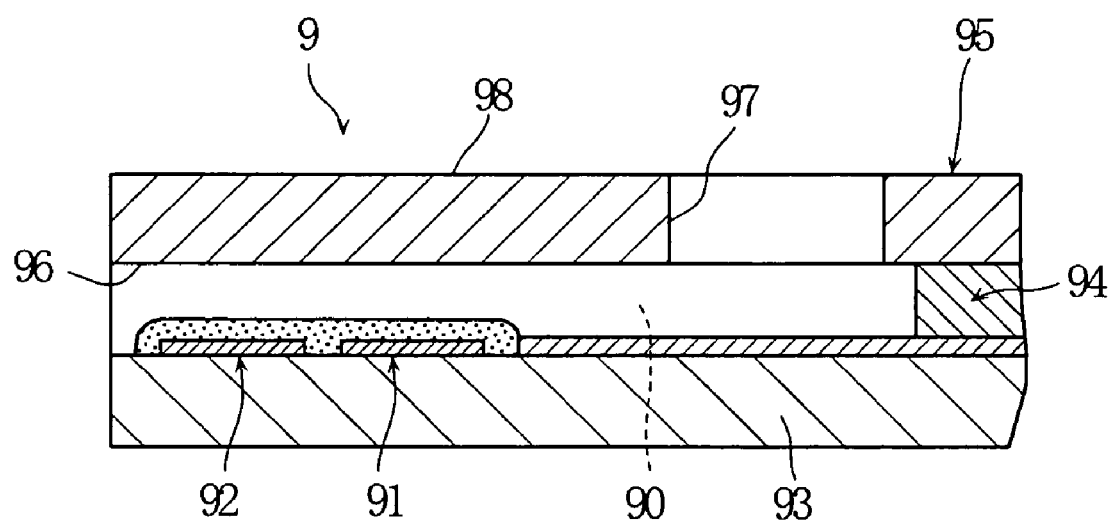
FIG. 22 is a sectional view taken along lines XXII-XXII in FIG. 20.

The supply of blood to the glucose sensor X1 can be performed either before or after the glucose sensor X1 is mounted to the blood glucose level measurer (not shown) . Generally, the blood supply is performed by cutting skin of a subject to extract blood and then applying the blood to the introduction port 40 of the glucose sensor X1. In the glucose sensor X1, the exhaust port 31 opens laterally as a part of the projection 30. Therefore, as compared with the structure of the conventional glucose sensor 9 (See FIGS. 20-22) in which the exhaust port 97 opens upward, the possibility that the blood is introduced erroneously through the exhaust port 31 instead of the introduction port 40 is small.

When the glucose sensor X1 is mounted to the blood glucose level measurer (not shown), the working electrode 11 and the counter electrode 12 of the glucose sensor X1 come into contact with the terminals (now shown) of the blood glucose level measurer. In the glucose sensor X1, the blood applied to the introduction port 40 moves toward the exhaust port 31 due to the capillary phenomenon occurring in the capillary 4. As the blood travels, the reagent portion 14 is dissolved by the blood, and a liquid phase reaction system is established in the capillary 4.

For instance, in the liquid phase reaction system, the oxidoreductase reacts specifically with glucose in blood to extract an electron from glucose, and the electron is supplied to the electron mediator, whereby the electron mediator becomes the reduced form. When a voltage is applied to the liquid phase reaction system by utilizing the working electrode 11 and the counter electrode 12, electrons are supplied from the electron mediator in the reduced form to the working electrode 11. In the blood glucose level measurer, when a voltage is applied to the working electrode 11 and the counter electrode 12, the amount of electrons supplied to the working electrode 11, for example, can be measured as the response current. In the blood glucose level measurer (not shown), the blood glucose level is computed based on the response current measured when a predetermined time period has lapsed from the supply of blood to the capillary 4.

The above-described glucose sensor X1 can be manufactured through a first plate formation step, an electrode formation step, an insulating film formation step, a reagent portion formation step, an intermediate product formation step and a cutting step. The first plate formation step can be performed after the electrode formation step, the insulating film formation step and the reagent portion formation step or simultaneously with these process steps.

Figure 4:
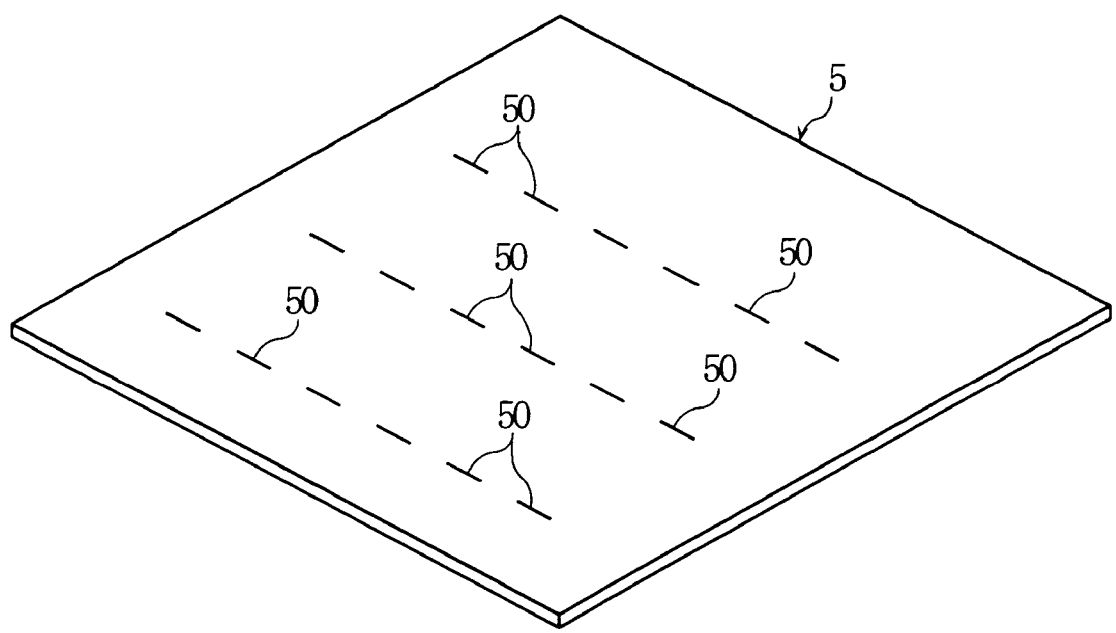
FIG. 4 is an overall perspective view of a flat plate formed with cuttings for describing a first plate formation step in a method for manufacturing the glucose sensor shown in FIGS. 1-3.
Figure 5A:
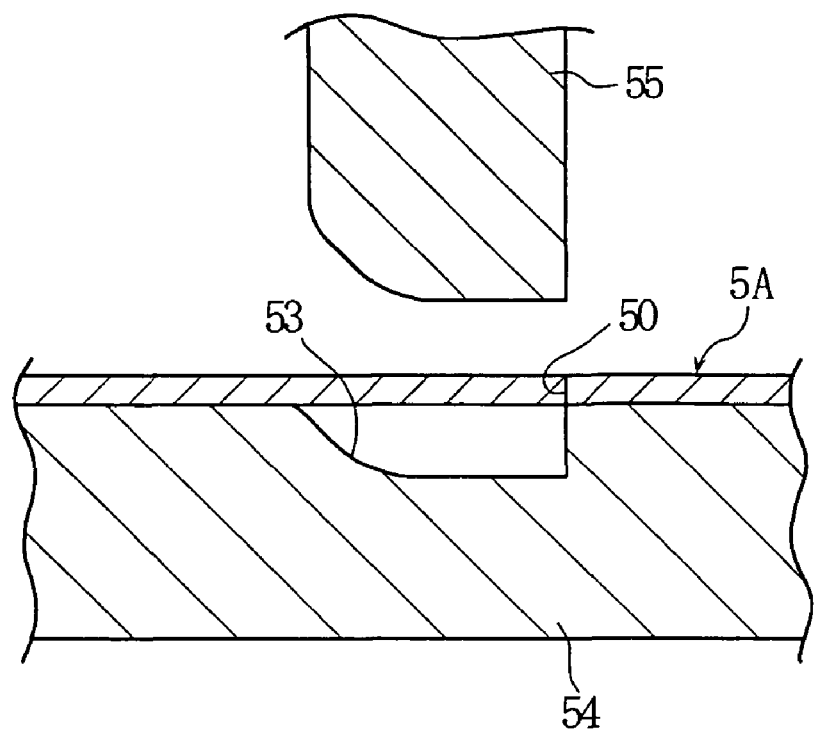
FIG. 5 includes a sectional view of a principal portion for describing the first plate formation step in the manufacturing method.
Figure 5B:
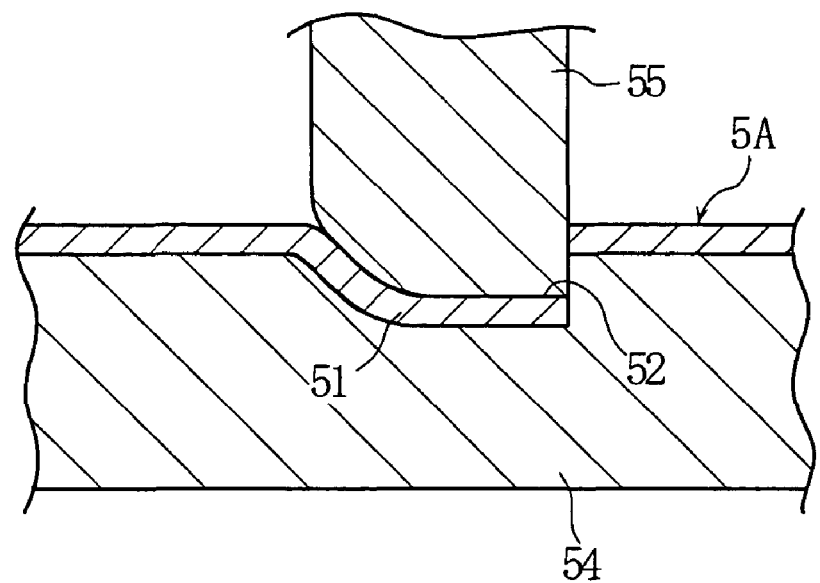
Figure 6:
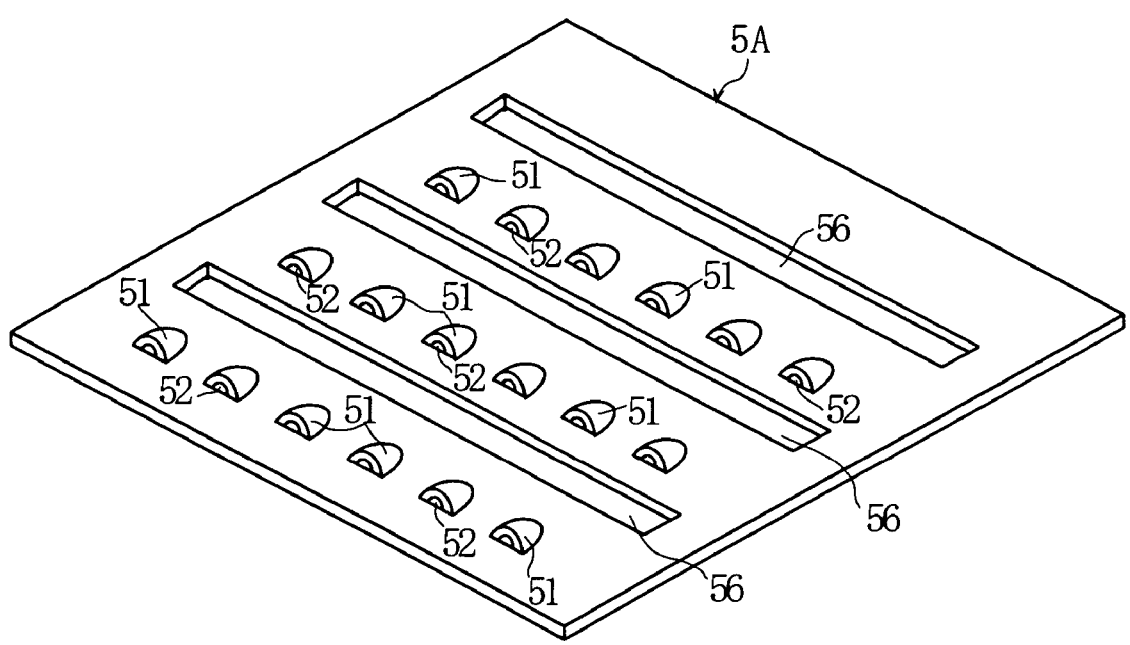
FIG. 6 is an overall perspective view showing the first plate after the first plate formation step is finished.

Firstly, in the first plate formation step, a plurality of cuts 50 are formed in a flat plate 5, as shown in FIG. 4. As the flat plate 5, one made of a thermoplastic resin such as vinylon may be used, and the cuts 50 can be formed by a known technique. Subsequently, as shown in FIGS. 5A and 5B, a plurality of projections 51 including openings 52 are formed by utilizing the cuts 50, whereby the first plate 5A as shown in FIG. 6 is obtained. Specifically, as shown in FIG. 5A, a bending die 54 formed with a recess 53 corresponding to the shape of the projection 51 to be formed is prepared, and the flat plate 5 is placed on the bending die 54 so that the cut 50 is located on the recess 53. Preferably, the bending die 54 is heated in advance to such a degree that the flat plate 5 becomes thermally deformable but is not melted. Subsequently, as shown in FIG. 5B, a punch 55 is positioned above the recess 53 and moved downward, whereby a projection 51 having an outer surface configuration corresponding to the inner surface configuration of the recess 53 is formed at the flat plate 5. The projection 51 thus formed includes an opening 52 which opens laterally at a portion offset from the flat plate portion of the first plate 5A in the thickness direction.

In the first plate formation step, openings 56 (See FIG. 11) are also formed which serve to expose the ends 61b and 62b of the working electrode 61 and the counter electrode 62 (See FIG. 7) to be formed later. The openings 56 may be formed at the same time as forming the cuts 50 or the projections 51 or may be formed separately from the cuts 50 or the projections 51.

The first plate formation step may be performed also by resin molding. Specifically, the first plate 5A can be formed by resin molding using a die capable of forming the projection 51, the opening 52 and the opening 56.

Figure 7:
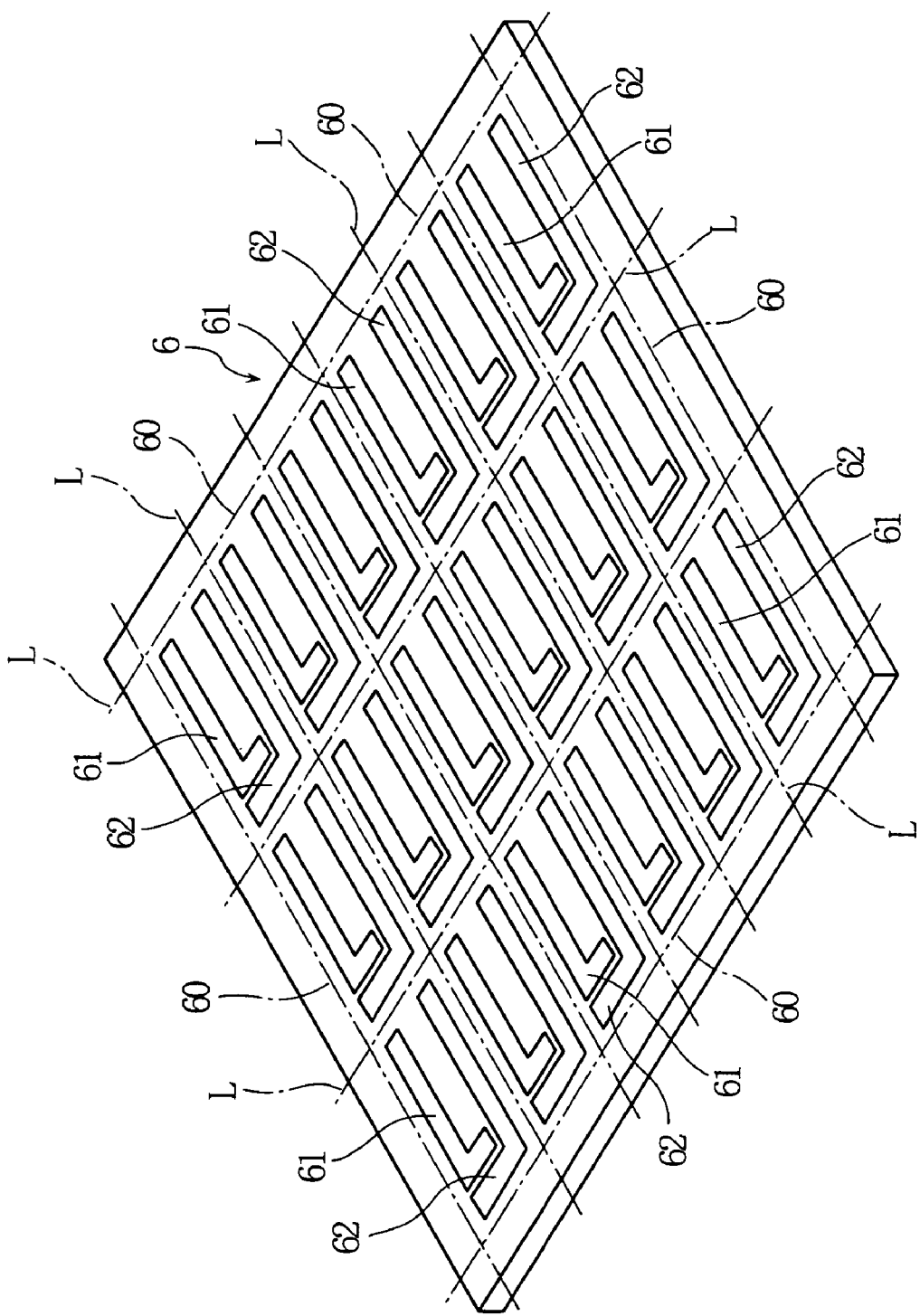
FIG. 7 is an overall perspective view showing a second plate after an electrode formation step is finished in the manufacturing method.

As shown in FIG. 7, in the electrode formation step, a working electrode 61 and a counter electrode 62 are formed at each of a plurality of sensor formation regions 60 set in a second plate 6. The formation of the working electrode 61 and the counter electrode 62 can be performed collectively with respect to a plurality of sensor formation regions 60 by screen printing using carbon paste, for example. The working electrode 61 and the counter electrode 62 can be formed by using a conductive material other than carbon and also by vapor deposition, sputtering or CVD.

Figure 8:
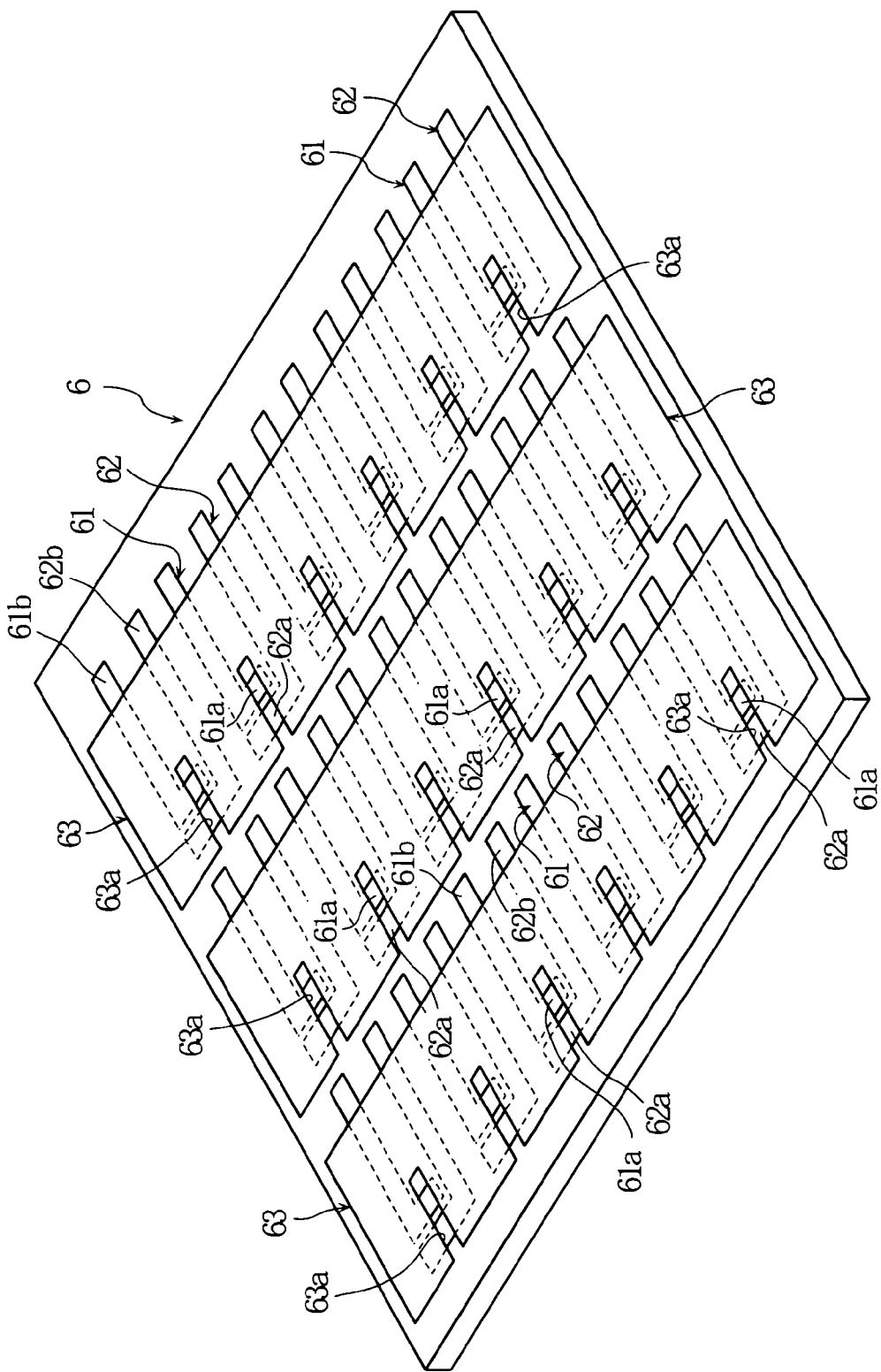
FIG. 8 is an overall perspective view showing a second plate after an insulating film formation step is finished in the manufacturing method.

As shown in FIG. 8, in the insulating film formation step, an insulating film 63 is formed on the second plate 6. The insulating film 63 includes a plurality of openings 63a each corresponding to the opening 13a (See FIG. 4) of the glucose sensor X1. The insulating film is so formed as to expose the ends 61a, 61b, 62a and 62b of the working electrode 61 and the counter electrode 62. The insulating film 63 can be formed by screen printing using ink containing a water-repellent material. Alternatively, the insulating film 63 can be formed by photolithography using a photosensitive resin.

Figure 9:
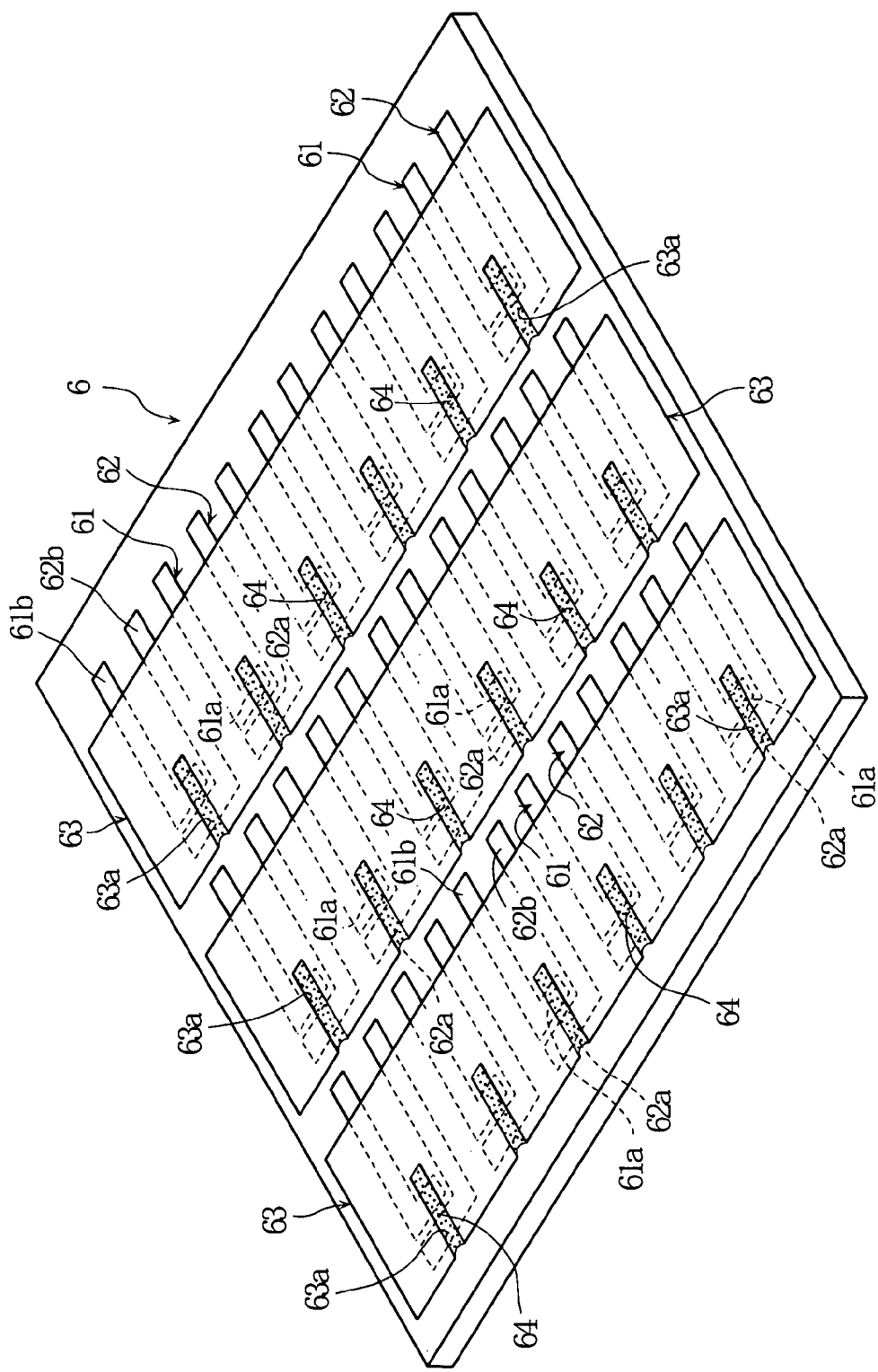
FIG. 9 is an overall perspective view showing a second plate after a reagent portion formation step is finished in the manufacturing method.

As shown in FIG. 9, in the reagent portion formation step, a reagent portion 64 is formed at each of the openings 63a of the insulating film 63. The reagent portion 64 can be formed by dispensing a material liquid containing an oxidoreductase and an electron mediator to each of the openings 63a and then drying the material liquid.

Figure 10:
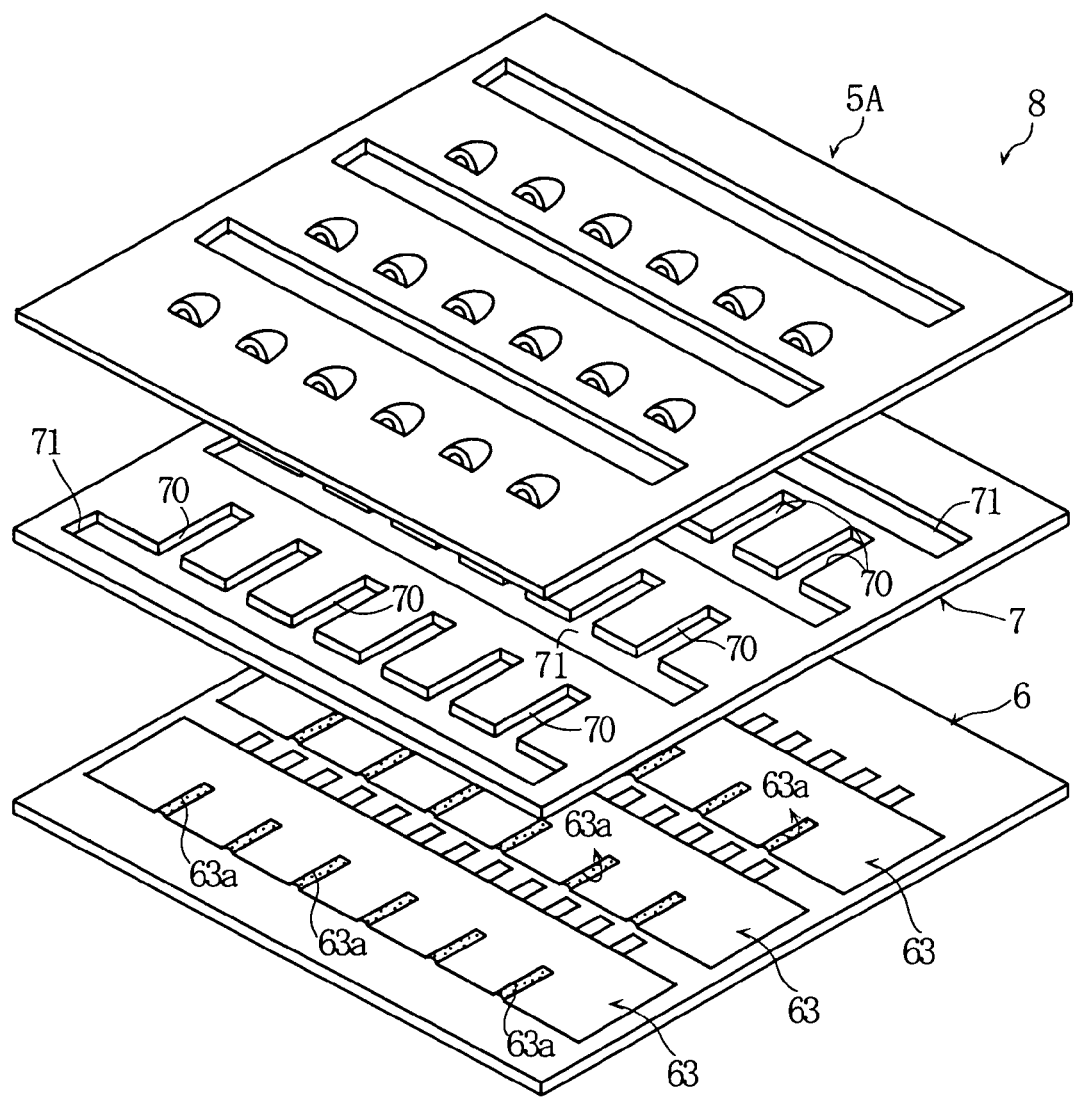
FIG. 10 is an overall perspective view for describing an intermediate product formation step in the manufacturing method.
Figure 11:
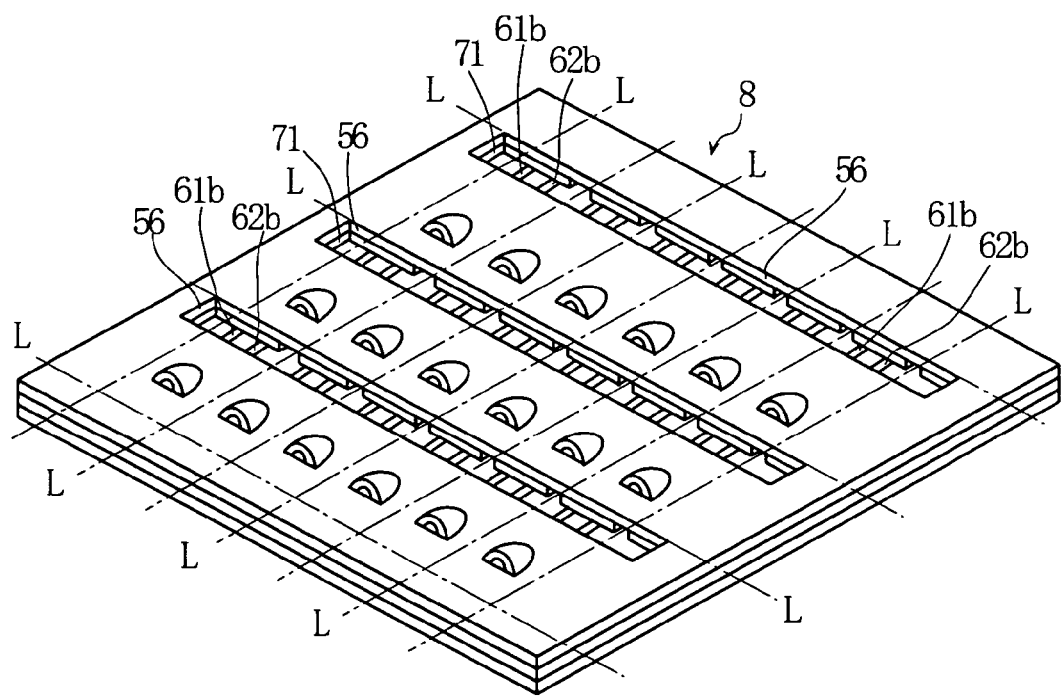
FIG. 11 is an overall perspective view showing the intermediate product after the intermediate product formation step is finished in the manufacturing method.

As shown in FIGS. 10 and 11, in the intermediate product formation step, an intermediate product 8 is formed by laminating the first plate 5A to the second plate 6 via a double-sided tape 7. The double-sided tape 7 is formed, in advance, with a plurality of openings 70 each of which is to become a slit 20 (See FIG. 2) and openings 71 (See FIG. 11) which serve to expose the ends 61b and 62b of the working electrode 61 and the counter electrode 62 (See FIG. 7). The double-sided tape 7 is interposed between the first plate 5 and the second plate 6, with the openings 70 positioned on the openings 63a of the insulating film 63 and the openings 71 positioned to expose the ends 61b and 62b of the working electrodes 61 and the counter electrodes 62.

In the cutting step, the intermediate product 8 is cut by utilizing the border lines between the sensor formation regions 60 as the cutting lines L (See FIG. 11), whereby individual glucose sensors X1 as shown in FIGS. 1-3 are obtained.

In the manufacturing method described above, the exhaust port 31 of the glucose sensor X1 is formed by press-working the flat plate 5. Therefore, unlike the conventional structure, a punched-out piece is not produced by the formation of the exhaust port 31. Therefore, such a situation that the cutout piece exists between the cover 3 and the substrate 1 so as to be exposed in the capillary 4 can be avoided. As a result, the deterioration of the measurement accuracy caused by the cutout piece can be prevented. Moreover, since the punched-out piece is not produced in forming the exhaust port 31, disposal of the punched-out piece is not necessary. Therefore, according to this embodiment, the manufacturing efficiency of the glucose sensor X1 can be enhanced.

The advantages of the above-described embodiment can be obtained also by the glucose sensor and the manufacturing method according to a second and a third embodiments described below.

The second embodiment of the present invention will be described with reference to FIGS. 12-15. In these figures, the elements which are identical or similar to those shown in the figures referred to in the first embodiment are designated by the similar reference signs.

Figure 12:
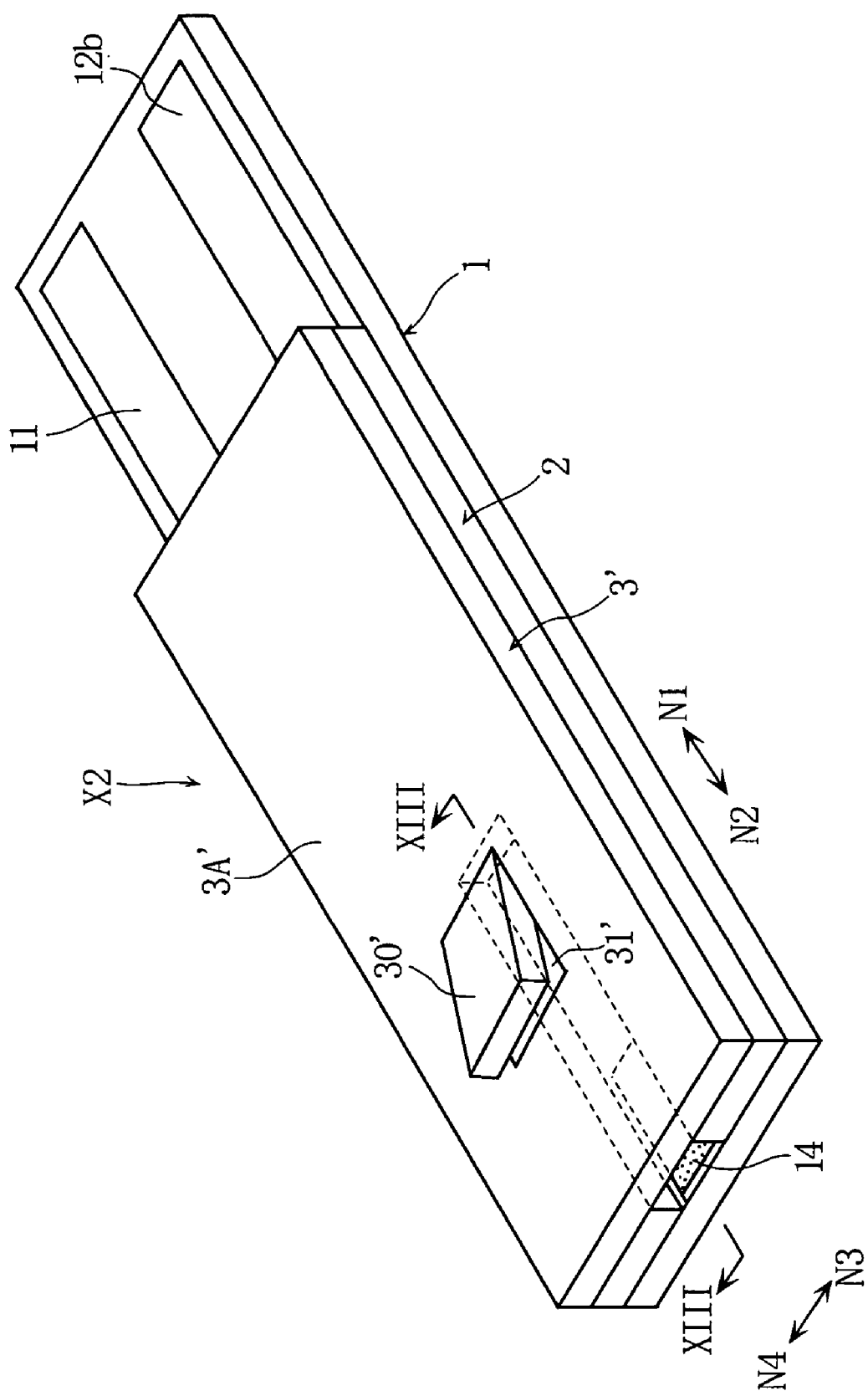
FIG. 12 is an overall perspective view showing a glucose sensor according to a second embodiment of the present invention.
Figure 13:
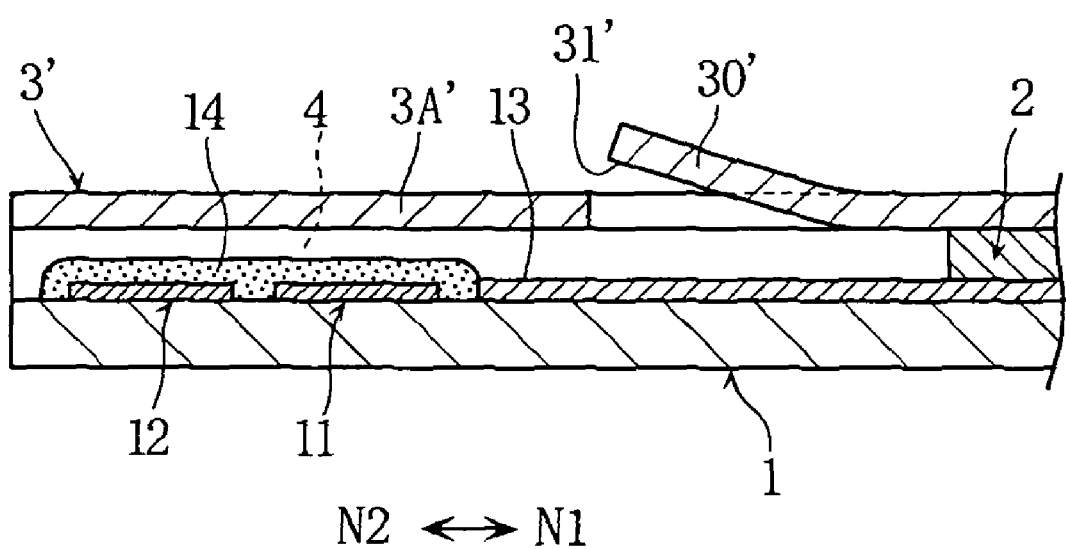
FIG. 13 is a sectional view taken along lines XIII-XIII in FIG. 12.

The glucose sensor X2 shown in FIGS. 12 and 13 differs from the foregoing glucose sensor X1 (See FIGS. 1-3) in structure of the cover 3'. Specifically, the cover 3' includes an exhaust port 31' provided by forming a cut-and-raised piece 30' in the cover. The exhaust port 31' includes a portion which opens in the directions indicated by arrows N2, N3 and N4 at a portion offset from the main body 3A' of the cover 3' in the thickness direction.

The glucose sensor X2 can be formed by performing the first plate formation step of the manufacturing method described in the first embodiment by the technique described below.

Figure 14A:
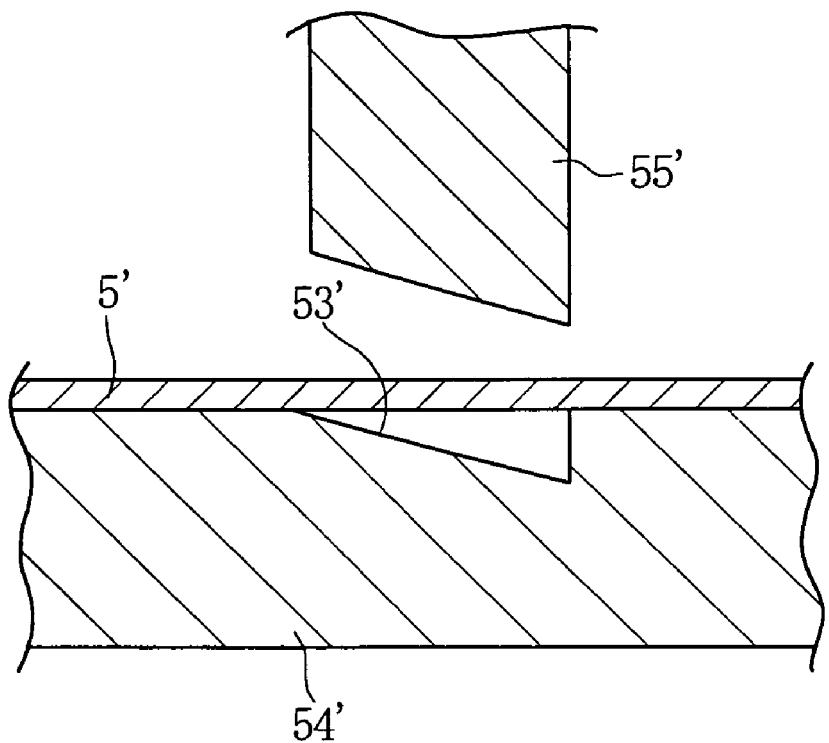
FIG. 14 includes a sectional view of a principal portion for describing the first plate formation step in a method for manufacturing the glucose sensor shown in FIGS. 12 and 13.
Figure 14B:
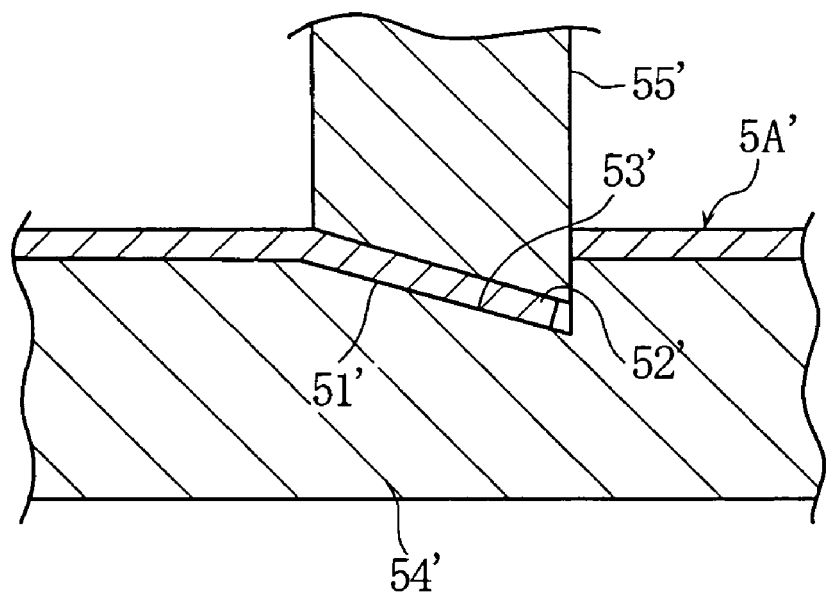
Figure 15:
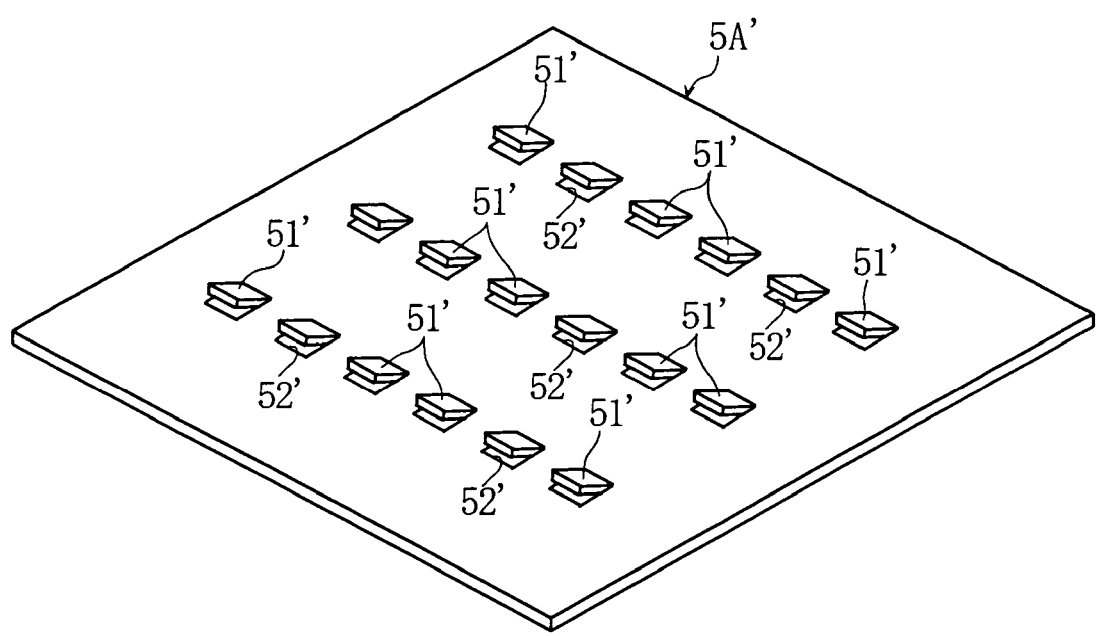
FIG. 15 is an overall perspective view showing the first plate after the first plate formation step is finished.

In the first plate formation step of this embodiment, a flat plate 5' is subjected to press working using a bending die 54' and a punch 55' shown in FIGS. 14A and 14B, whereby a first plate 5A' as shown in FIG. 15 is obtained. Specifically, in the first plate formation step, the flat plate 5 is placed on the bending die 54' formed with a recess 53' having a triangular cross section. In this state, the punch 55' having a sharp edge is positioned above the recess 53' and moved downward. As a result, as shown in FIGS. 14B and 15, part of the flat plate 5' is cut and raised, whereby the first plate 5A40 formed with cut-and-raised pieces 51' and openings 52' is obtained.

Next, the third embodiment of the present invention will be described with reference to FIGS. 16-19. In these figures, the elements which are identical or similar to those shown in the figures referred to in the first embodiment are designated by the similar reference signs.

Figure 16:
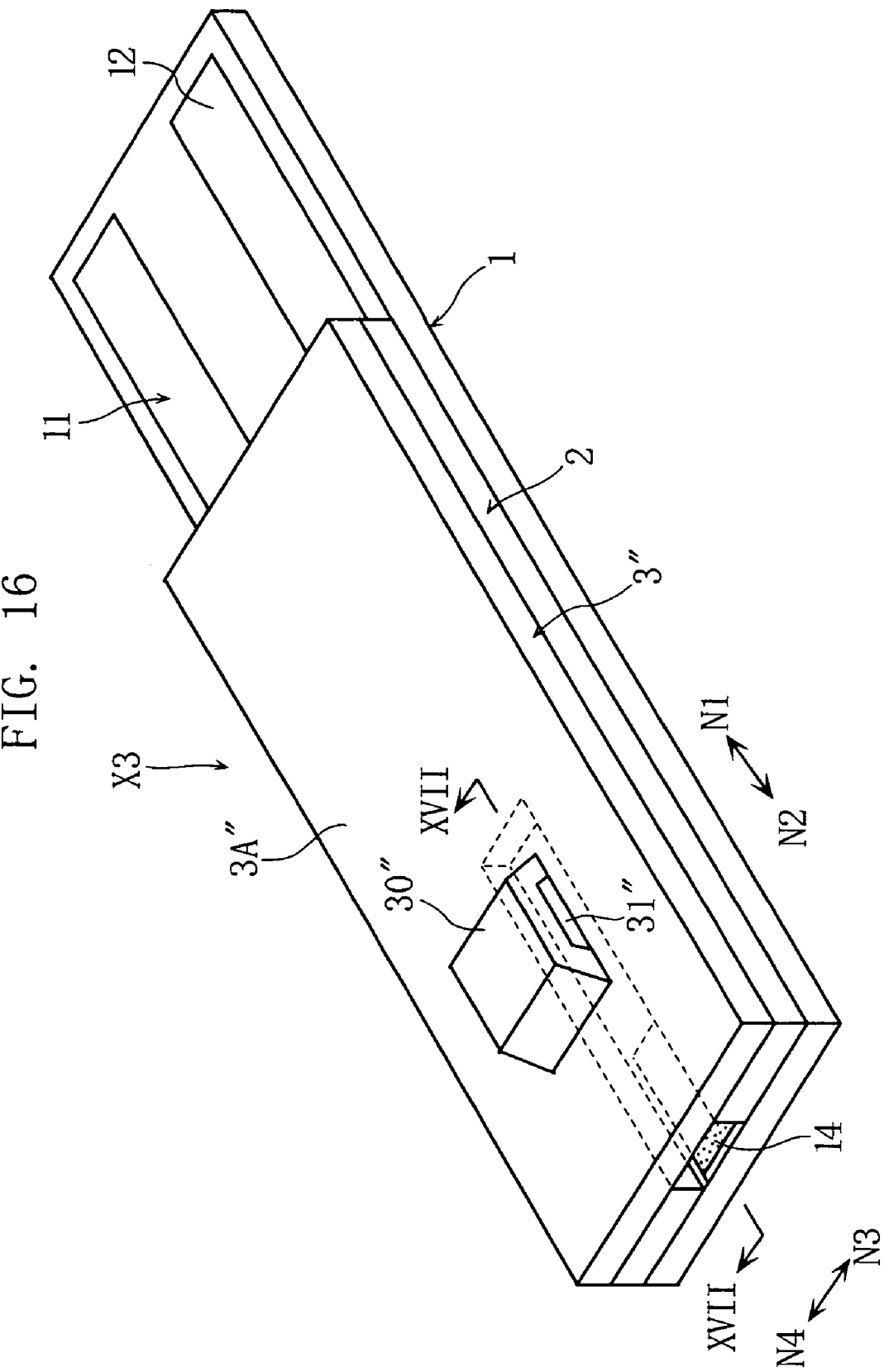
FIG. 16 is an overall perspective view showing a glucose sensor according to a third embodiment of the present invention.
Figure 17:
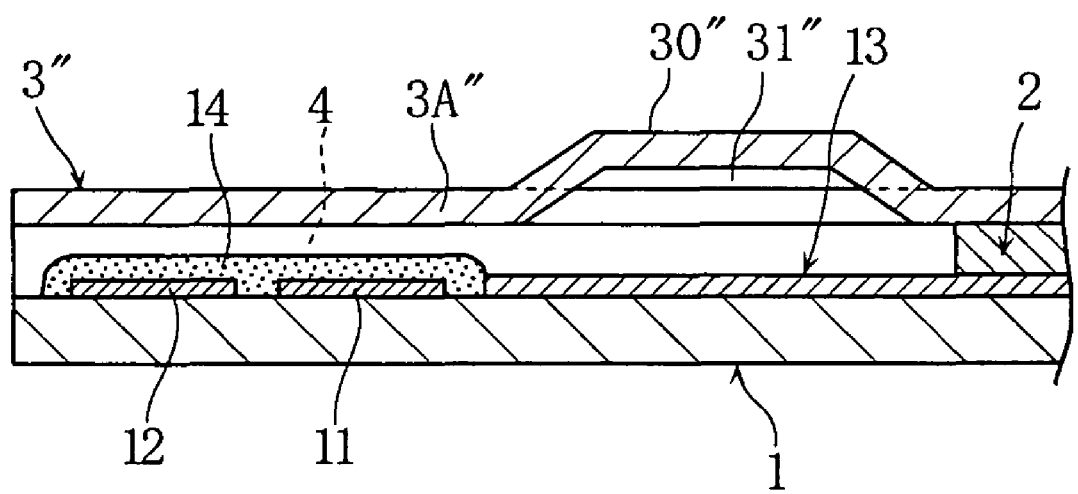
FIG. 17 is a sectional view taken along lines XVII-XVII of FIG. 16.

The glucose sensor X3 shown in FIGS. 16 and 17 differs from the foregoing glucose sensor X1 (See FIGS. 1-3) in structure of the cover 3'. Specifically, the cover 3' includes an exhaust port 31" which is provided by forming a projection 30" shaped like a bridge at a portion of the cover. At a position offset from the main body 3A" of the cover 3" in the thickness direction, the exhaust port 31" includes a portion which opens in the direction indicated by arrow N3 as shown in FIG. 16 and a portion which opens in the direction indicated by arrow N4 as shown in FIG. 17.

The glucose sensor X3 can be formed by performing the first plate formation step of the manufacturing method described in the first embodiment by the technique described below.

Figure 18A:
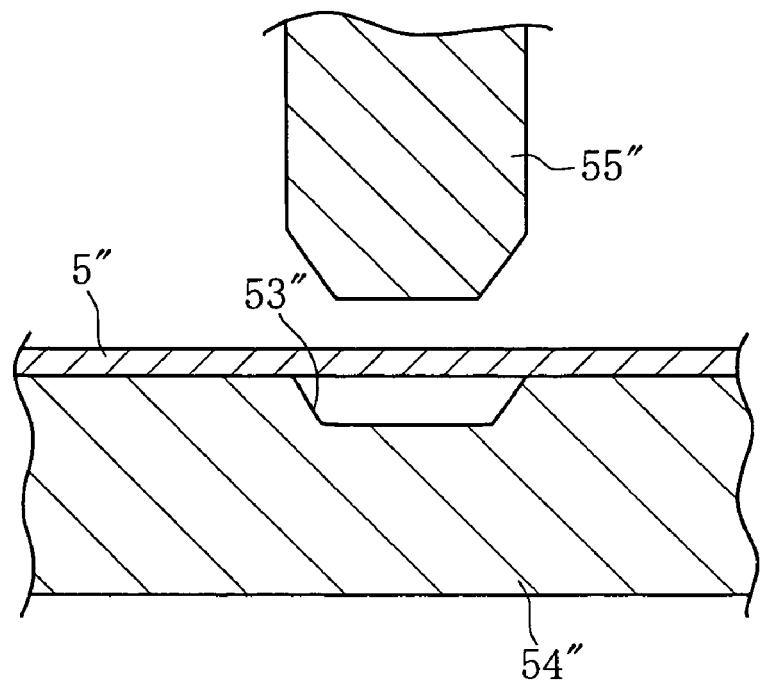
FIG. 18 is a sectional view of a principal portion for describing a first plate formation step in a method for manufacturing the glucose sensor shown in FIGS. 16 and 17.
Figure 18B:
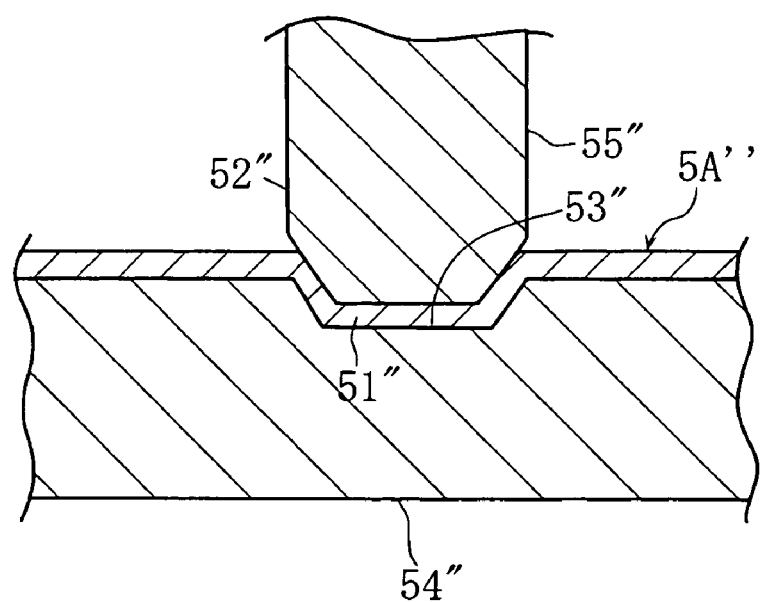
Figure 19:
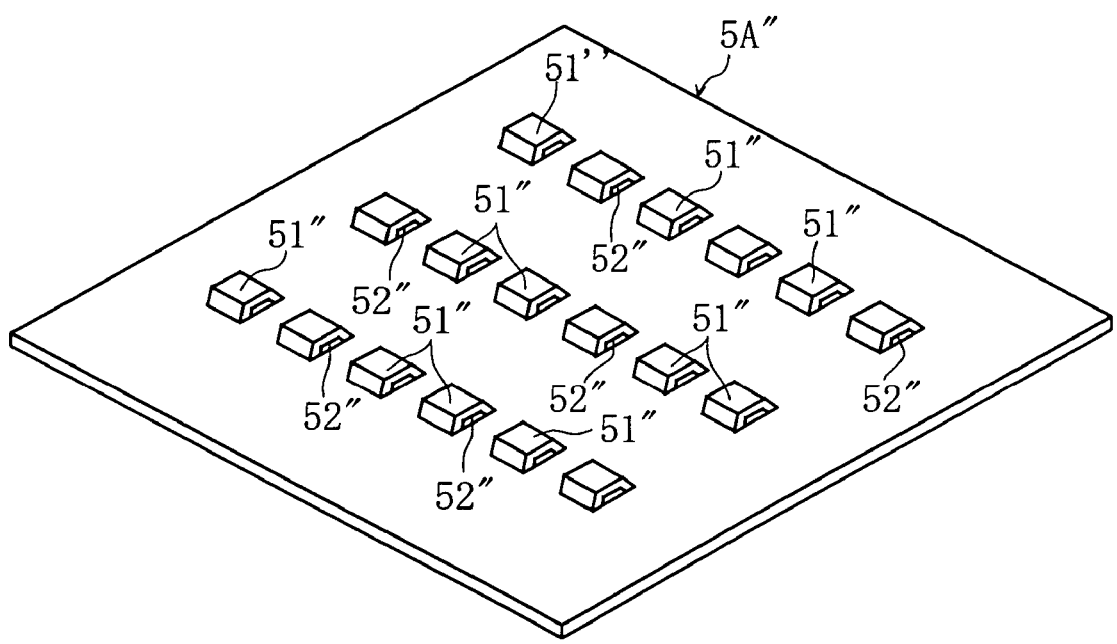
FIG. 19 is an overall perspective view showing a first plate after the first step is finished.

In the first plate formation step of this embodiment, a flat plate 5" is subjected to press working using a bending die 54" and a punch 55" shown in FIGS. 18A and 18B, whereby a first plate 5A" as shown in FIG. 19 is obtained. Specifically, in the first plate formation step, the flat plate 5" is placed on the bending die 54" formed with a recess 53" having a trapezoidal cross section. In this state, the punch 55' having an end corresponding to the inner surface configuration of the recess 53" is positioned above the recess 53" and moved downward.

The present invention is not limited to the glucose sensors described in the first through the third embodiments and may be varied in various ways. Particularly, the direction in which the exhaust port opens is not limited to those exemplarily described above. For instance, although the exhaust port 31 of the glucose sensor X1 according to the first embodiment opens in the direction indicated by arrow N2, the exhaust port may open in the direction indicated by arrow N1, N3 or N4.

The present invention is not limited to a glucose sensor which is designed to measure the glucose level in blood by an electrochemical technique, and is also applicable to other analytical tools. Examples of analytical tool to which the present invention is applicable include one designed for measuring a component in blood other than glucose (e.g. lactic acid or cholesterol), one designed for performing analysis by using a sample other than blood and one designed for analyzing a particular component (e.g. glucose, lactic acid or cholesterol) contained in a sample (e.g. blood or urine) by an optical technique.

The invention claimed is:

1. An analytical tool comprising a first and a second plate elements, a flow path defined between the plate elements and including a sample introduction port, and an exhaust port for discharging gas from the flow path,
the first plate element including a flat main body,
the exhaust port being provided on the first plate element and including an offset portion which is offset in a thickness direction of the main body, the offset portion of the exhaust port is located above the flow path, with the first plate element being present in a plane between the offset portion and the flow path,
wherein the offset portion of the exhaust port is located higher than the sample introduction port.

2. The analytical tool according to claim 1, wherein the offset portion projects from the main body and is integrally formed on the main body for defining the exhaust port.

3. The analytical tool according to claim 2, wherein the offset portion is provided by deforming part of the first plate element.

4. The analytical tool according to claim 2, wherein the offset portion comprises a cut-and-raised piece.

5. The analytical tool according to claim 2, wherein the offset portion is in a form of a dome.

6. The analytical tool according to claim 5, wherein the offset portion includes at least one opening to serve as the exhaust port.

7. The analytical tool according to claim 2, wherein the offset portion is in a form of a bridge.

8. The analytical tool according to claim 7, wherein the offset portion includes a pair of openings which open in a horizontal direction and serve as the exhaust port.

9. A method of manufacturing an analytical tool, the method comprising:
a first step of forming a first plate member including a flat main body and an exhaust port including an offset portion which opens at a position offset in a thickness direction of the main body; and
a second step of bonding a second plate member to the first plate member at a predetermined distance for forming a flow path defined between the first plate member and the second plate member, the flow path including a sample introduction port;
wherein the offset portion of the exhaust port is located above the flow path, with the first plate member being present in a plane between the offset portion and the flow path,
and the offset portion of the exhaust port is located higher than the sample introduction port.

10. The method of manufacturing an analytical tool according to claim 9, wherein said exhaust port is formed by press working a flat plate.

11. The method of manufacturing an analytical tool according to claim 10, wherein the flat plate is a plate made of a thermoplastic resin; and
wherein the press working is performed with the flat plate heated to be thermally deformable.

12. The method of manufacturing an analytical tool according to claim 10, wherein, in the press working, part of the flat plate is cut and raised to form said exhaust port.

13. The method of manufacturing an analytical tool according to claim 10, wherein the first step comprises forming a cut in the flat plate before the press working is performed.

14. The method of manufacturing an analytical tool according to claim 13, wherein the flat plate is a plate made of a thermoplastic resin; and
wherein the press working comprises compressing a portion adjacent to the cut for thermal deformation with the flat plate heated to be thermally deformable.

* * * * *